(12) United States Patent
Sakurai et al.

(10) Patent No.: US 7,241,814 B2
(45) Date of Patent: Jul. 10, 2007

(54) PREPARATION OF METALLIC NANOPARTICLES WITH SHELL-CROSSLINKED MICELLE AS MOLD

(75) Inventors: Hideki Sakurai, Miyagi (JP); Takanobu Sanji, Kanagawa (JP)

(73) Assignee: Japan Science and Technology Agency, Saitama-ken (JP)

( * ) Notice: Subject to any disclaimer, the term of this patent is extended or adjusted under 35 U.S.C. 154(b) by 362 days.

(21) Appl. No.: 10/491,133
(22) PCT Filed: Jul. 12, 2002
(86) PCT No.: PCT/JP02/07118

§ 371 (c)(1),
(2), (4) Date: Mar. 29, 2004

(87) PCT Pub. No.: WO03/039793

PCT Pub. Date: May 15, 2003

(65) Prior Publication Data

US 2004/0259154 A1    Dec. 23, 2004

(30) Foreign Application Priority Data

Nov. 9, 2001 (JP) .............................. 2001-344048

(51) Int. Cl.
- *B01J 13/00* (2006.01)
- *B29B 13/00* (2006.01)
- *G01N 33/53* (2006.01)
- *C01G 7/00* (2006.01)

(52) U.S. Cl. .................. 516/100; 516/97; 428/407; 264/7; 524/588; 977/777

(58) Field of Classification Search ............... 516/97, 516/100; 264/225, 7; 428/407; 977/777; 524/588

See application file for complete search history.

(56) References Cited

U.S. PATENT DOCUMENTS 4,347,304 A * 8/1982 Sakurai et al. .............. 430/291
4,808,659 A * 2/1989 Nishihara et al. ........... 524/701
6,491,903 B1 * 12/2002 Forster et al. ............... 428/407
2004/0228823 A1 * 11/2004 Bronich et al. ........... 424/70.16

FOREIGN PATENT DOCUMENTS

JP    11271981 A    * 10/1999
JP    2001-200180 A    * 7/2001

OTHER PUBLICATIONS

Derwent Abstract on EAST, week 200613, London: Derwent Publications Ltd., AN 2002-057680, JP 2001-200180 A, (Shinetsu Chem Ind Co Ltd), abstract.*

(Continued)

*Primary Examiner*—Daniel S. Metzmaier
(74) *Attorney, Agent, or Firm*—Hahn & Voight PLLC

(57) ABSTRACT

A method for the preparation of a dispersion of fine particles characterized in that the micelles are ones which have been formed in a aqueous medium with an amphiphilic block copolymer represented by the general formula PB and in which the shell of each micelle has been cross-linked with hydrophilic groups of the hydrophilic side chains wherein the particles formed are metallic particles having a reducing characteristic of metal ions. The general formula PB is:

general formula PB

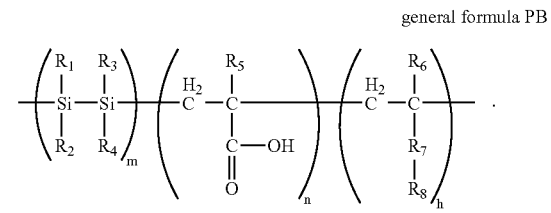

9 Claims, 3 Drawing Sheets

OTHER PUBLICATIONS

Derwent Abstract on EAST, week 200357, London: Derwent Publications Ltd., AN 1999-623399, JP 11271981 A, (Shinetsu Chem Ind Co Ltd), abstract.*

T. Sanji et al. "Encapsulation of polysilane into shell cross-linked micelles", Cemical Communications, The Royal Society of Chemistry, 1999, pp. 2201-2202 (Month unknown).*

T. Sanji et al, "Preparation of Nanometer-Sized Hollow Particles by Photochemical Degradation of Polysilane Shell Cross-linked Micelles and Reversible Encapsulation of Guest Molecules", Macromolecules 2000, V. 33, 8524-8526, (month unknown).*

* cited by examiner

PREPARATION OF METALLIC NANOPARTICLES WITH SHELL-CROSSLINKED MICELLE AS MOLD

FIELD OF THE INVENTION

The present invention relates to a method for preparation of monodispersed particles of metal such as gold, platinum, palladium or silver by following process. That is, after forming a micelle possessing a constitutive unit having polysilane in inside in aqueous medium using block copolymer of hydrophilic polymer and silane, preparing shell-cross linked micelle by cross linking a shell part of the micelle by a cross-linking agent then preparing monodispersed particles of gold, platinum, palladium or silver, of nano size using said micelle utilizing a reducing characteristic of metallic ion of said metals locating at the main chain of polysilane and a template characteristic of the micelle.

BACKGROUND OF THE INVENTION

The fine particles of a metal, in particular, fine particles of gold, platinum, palladium, rhodium or silver have a possibility to be used as a medicine utilizing penetrating ability of an ultra fine particles into reticuloendothelial system, an inspection agent with function, material for Drug Delivery System (DDS), an improving material for detection sensitivity at the analysis utilizing the surface sensitization effect by resonance Raman scattering, and methods for preparation of dispersion of said metals which does not coagulate and is stable are presently being investigated.

In the above mentioned circumstance, as the substantial methods for the preparation of nano size particles e.g. gold up to the present time, following 1-4 methods are proposed.

1. The method to reduce metallic ion by coexisting surfactant or polymer.

This method is characterized by coexisting surfactant or polymer in the reducing reaction medium aiming to prevent the flocculation of metal generated by the reduction of the metallic ions and to stabilize the fine particles of metal generated by the reduction of metallic ions. This method is characterized by coexisting surfactant or polymer with metallic ions and using reducing agent such as sodium borohydride ($NaBH_4$) separately from the reduction by light irradiation from the outside. According to this method, although the reduction of various metals can be possible, the problem that it is necessary to add a reducing agent for each metal ions separately is pointed out. [Document 1; Schmid, Chem. Rev., 92, 1709 (1992)].

2. Method for stabilizing using gold/sulfur reciprocal action This method is the method for stabilizing of fine particles of gold generated by reduction utilizing strong affinity between sulfur and gold, by bonding fine particles of gold electrostatically with sulfur atom. In this case, the sulfur atom which displays above mentioned function can be provided by introducing a group having said molecule at the end or side chain of a unit of arbor shape molecule (dendron) or polymer. It is known that a DNA molecule is also effective for the stabilization of fine particles of gold instead of above stabilizing substance. The merit of this method is that the surface of metal particle can be modified by various organic compound, especially by a compound having desired functional group, however, it is not effective to the metals except gold. [Document 2; M. Brust, M. Walker, D. Betheli, D. J. Schiffrin, and R. Whyman, Chem. Commum, 1994, 801. Document 3; V. Chechik and R. M. Crooks, Langmuir 15, 6364 (1994). Document 4; M.-K. Kim, Y.-M. Joen, H.-J. Kim, S. G. Hong, C. G. Park, and K. Kim, Chem. Commum, 2001, 667.)].

3. Method for preparation of fine particles of metal using dendrimer as a template This method is the method for preparation of fine particles of metal of several ten nm size using water soluble poly (amide amine) dendrimer, characterized by using a reducing agent such as sodium borohydride ($NaBH_4$) after metal ions are introduced into the dendrimer. [Document 5; M. Zhao, L. Sun and R. M. Crooks, J. Am. Chem. Soc, 120, 4877 (1998). Document 6; L. Balogand D. A. Tomalia, J. Am. Chem. Soc., 120, 7355 (1998). Document 7; Y. Nie, L. K. Yeung and M. Crooks. J. Chem. Soc., 123, 6840-6846. Document 8; L. K. Yeung and M. Crooks. Nano Lwtt., 1, 14-17 (2001.)].

The merit of this method is that the fine particles of metal obtained by reduction of metallic ions can be of monodispersed particles with narrow distribution based on the function of the template, however, it is necessary to add a reducing agent.

On the contrary,

4. The method to obtain the stabilized dispersion of fine particles of metal by reducing metallic ions utilizing the reducing ability of poly(dithiafulvene) and dispersion stabilizing ability of fine particles of metal is known. This method is to reduce metallic (golden) ions to fine particles of metal by stirring effectively polythiafulvene and metallic (golden) ions in dimethylsulfoxide. By this method it is not necessary to add reducing agent of metal from the outside, and utilizing the reducing ability which the polymer originally has, and this is the characteristic of this method (Document 9; Y Zhou, H. Itoh, T. Uemura, K. Naka and Y. Chujo, Chem. Commum., 2001, 613-614.). However, this method is necessary to carry out the reaction in dimethylsulfoxide, and since the generated fine particles of metal are stabilized by poly(dithiafulvene), the generated fine particles of metal are soluble in dimethylsulfoxide. And, the necessary use of dimethylsulfoxide as the medium, causes the problem to the environment.

The subject of the present invention is to provide a method for preparation of metallic nano particles which dissolve the problems which above mentioned prior arts have. Said problems can be illustrated as follows. Namely, the problem that the reducing agent for metal must be added beside the component which stabilize the metallic nano particles, and the problem that, when an inorganic reducing agent is not added separately, since it is necessary to use organic medium to obtain stabilized metallic nano particles, the obtained metallic nano particles can not be used for the reaction in water. In other words, the subject of the present invention is to provide a method for preparation of the metallic nano particles having the characteristic of monodispersion, which is possible to reduce metallic ions without using an inorganic reducing agent and using water as the medium, by generating metallic nano particles, which are stable in water, under coexisting of the material which has a characteristic of template.

The inventors of the present invention already proposed that the shell cross-linked micelle (SCM) can be synthesized by following process, that is, synthesizing block copolymer of polysilane, which is hydrophobic polymer, and polymethacrylic acid, which is hydrophilic polymer containing carbon, forming micelles in water based on the amphipathicity, then by cross-linking a carboxylic group of shell part of the polymer micelle by diamine compound. [Document 10; T. Sanji, Y Nakatsuka, F. Kitayama and H. Sukurai, Chem. Comun., 1999, 2201-2202. Document 11; T. Sanji, Y. Nakatsuka, S. Ohnishi and H. Sakurai. Macromolecules, 33. 8524-8526 (2000 Further, it is also well known that the shell cross-linked micelle is completely water soluble.

In the meanwhile, it is publicly known that polysilane has a reducing ability for metallic ions [Document 12; A. F. Diaz, M. Baier, G. M. Wallraff, R. D. Miller, J. Nelson, W. Piero, J. Electrochem. Soc. 138,742 (1991)], further, it is also publicly known that the metallic layer can be formed by utilizing said polysilane layer as a reducing ability of metallic ions such as Au, Ag, Pt or Pd for forming metallic layer [Document 13; M. Fukushima, N. Noguchi, M. Aramata, Y Hamada, E. Tabei, S. Mori and Y. Yamamoto. Syth. Met., 273-280 (1998)].

However, there is no technical paper reporting the method to obtain the dispersion of fine particles of metal by utilizing above mentioned reducing characteristic.

The inventors of the present invention have took notice of the reducing ability of the silane to the metallic ions which polysilane has, and the stabilizing ability and water solubility caused by the amphipathic polymer reported by the inventors of the present invention, tried to reduce the metallic ions such as gold, palladium or others in water using shell cross-linked micelle having constitutive unit of polysilane in inside as a template, and found that the dispersion of fine particles of metal having controlled particle size (monodispersion) of ten several to several ten nano meter size which are stable in aqueous medium can be obtained. And, the subject of the present invention can be dissolved.

DISCLOSURE OF THE INVENTION

The basic construction of the present invention is a method for preparation of monodispersed fine particles of metal comprising, reducing metallic ions by means of a reducing agent, wherein the reducing agent is hydrophilic micelle having polysilane which is obtained from the block copolymer composed of hydrophilic polymer and polysilane represented by general formula P-1 in inside of said micelle, and the shell part of the micelle is cross-linked.

general formula P-1

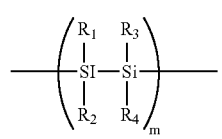

In general formula P-1, $R_1$, $R_2$, $R_3$ and $R_4$ are the group selected independently from the group consisting of alkyl group of carbon number 10 or less and aryl group, m is degree of polymerization. n is degree of polymerization of monomer component having cross-linking hydrophilic group of hydrophilic polymer forming block polymer and n is in the range of molecular weight of block polymer to be Mn=7000–30000 and is decided so as the ratio of n with degree of polymerization of polysilane n/m to be from 10 to 20 (m/n is from 0.05 to 0.10).

Desirably, the present invention is the method for preparation of dispersion of fine particles of metal, wherein the hydrophilic micelle is formed by forming a micelle in aqueous medium, using amphipathic block copolymer represented by general formula PB obtained by block copolymerization of anionic polymerizable monomer possessing polysilane and at least hydrophilic side chain with hydrophilic polymer containing hydrophilic polymer component, and cross-linking the shell of said micelle by hydrophilic group of the hydrophilic side chain.

general formula PB

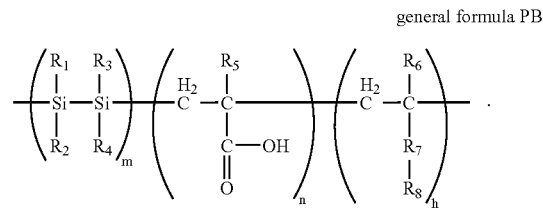

In general formula PB, $R_1$, $R_2$, $R_3$, $R_4$, m and n are same as to these of general formula P1. $R_5$ and $R_6$ are H or lower alkyl group, $R_7$ is a divalent organic group, —COOR— (wherein R is alkylene or phenylene group of carbon number 3 or less) or phenylene group, $R_8$ is COOH or OH group, h indicates copolymer component forming hydrophilic polymer with n', i.e., n'+h=n (general formula P1 is the case of h is 0) regarding the range from 0 to n, the value of n is in the range not hurting the hydrophilicity of the shell.

More desirably, the present invention is the method for preparation of dispersion of fine particles of metal, wherein the polysilane unit is represented by formula 1.

formula 1

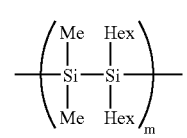

In the formula, Me is methyl group, Hex is hexyl group.

Further, in above mentioned methods for preparation of dispersion of fine particles of metal, wherein the cross-linking agent is the compound selected from the compounds represented by general formula B.

general formula B

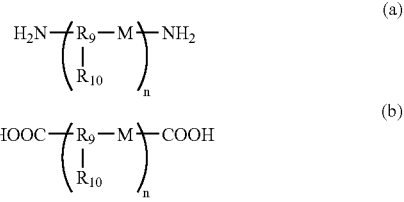

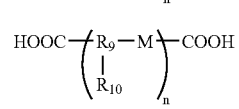

In general formula B, $R_9$ is alkylene chain of carbon number 4 or less, $R_{10}$ is functional group which substitute H of alkylene providing function to the obtained dispersion of fine particles of metal, n is from 2 to 30, M is oxygen, nitrogen or sulfur.

Desirably, the present invention is the method for preparation of dispersion of fine particles of metal, wherein the cross-linking agent represented by general formula B is poly(oxyalkylene), by establishing M as oxygen and establishing R as alkylene group of carbon number 4 or less.

BRIEF ILLUSTRATION OF THE DRAWINGS

DESCRIPTION OF THE PREFERRED EMBODIMENT

Figure 1:
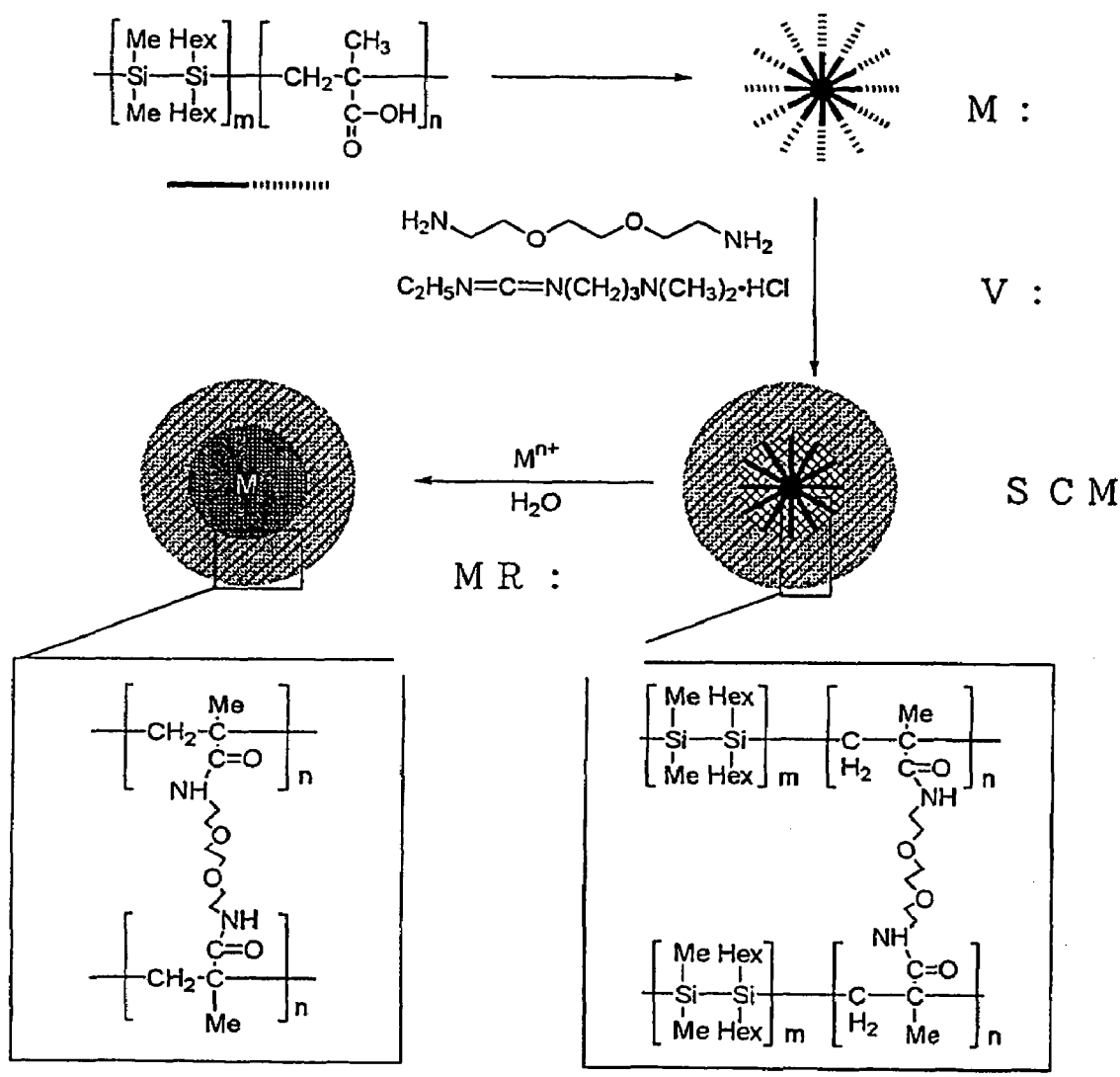
FIG. 1 is the plan view showing the preparation process of metallic nano particles of the present invention consisting of hydrophilic micelle forming process M, forming shell cross-kinked micelle by cross-linking process V of the hydrophilic micelle and preparation process of metallic nano particles by reduction of metal MR using above mentioned SCM as a template.

The present invention will be illustrated more in detail by following description.

A. In the present invention, as the block copolymer composed of hydrophilic polymer and polysilane used for the preparation of hydrophilic micelle utilized for the preparation of monodispersed dispersion of fine particles by reduction of metallic ion, the block copolymer composed of polysilane unit of general formula P1 and hydrophilic polymer, for example, homopolymer or copolymer containing a monomer possessing hydrophilic group such as acrylic acid or methacrylic acid can be used. Regarding such kind of block copolymer, the compound described in documents 10 and 11 which were reported by the inventors of the present invention, namely, poly(1,1-dimethyl-2,2-dihexyldisilanilene)-block-polymethacrylic acid (PSi-b-PMAA) can be mentioned for the reference.

Further, as the monomer possessing hydrophilic group, following compounds C can be exemplified.

compounds C

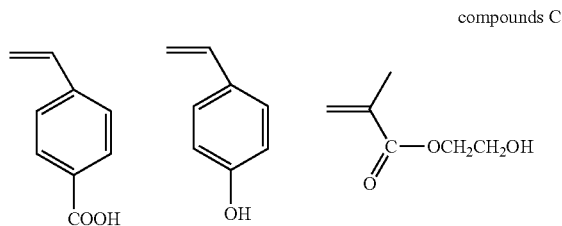

B. As the cross-linking agent for the shell of hydrophilic micelle, compound possessing a group which cross-links with side chain of hydrophilic polymer, for example, amino group or carboxyl group at the both ends, possessing an unit having oxygen, nitrogen or sulfur atom which bonds electrostatically with fine particles of metal to be formed, for example, polyoxyalkylene (alkylene of carbon number 2 to 4) at the bonding part of said end group and providing a functionality to the monodispersed fine particles of metal can be mentioned, for example, in the case of improvement at the use of analysis which is publicly known, polyalkylene derivatives possessing a functional group which bonds with analyzed component, or polyalkylene derivatives whose oxygen is substituted with a sulfur atom which improves the affinity with metal.

By changing the cross-linking agent or the ratio of polysilane and monomer possessing hydrophilic group of an unit of copolymers of general formulae P1 and PB, it is possible to cope with various solvents.

C. As the metallic ion used for the preparation of the monodispersed fine particles of metal of the present invention, the metallic ion described in the documents cited as the prior art. As the desirable one, halogenated auric acid, for example, tetrachloroaurate(III)tetrahydrate, halogenated platonic acid, silver nitrate and palladium chloride (II) can be exemplified, and the metallic ion can be selected voluntarily according to the usage of fine particles of metal.

EXAMPLES

The present invention will be illustrated specifically according to the following Examples, however, not intending to limit the scope of the present invention.

Example 1

Synthesis of poly(1,1-dimethyl-2,2-dihexyldisilanilene)-block-polymethacrylic acid 2.04 g ($4.97 \times 10^{-3}$ mol) of masked disilene and 20 mL of dried tetrahydrofuran were poured into a flask equipping septum rubber and a magnetic stirrer in a gloved box. The content in the flask is cooled down to the temperature lower than $-78°$ C., 0.72 mmol, 15 mol % of hexane solution of n-butyllithium was added, then the temperature was elevated to the room temperature and polymerized. The color of the solution turned to the red purple color. After stirred for 20 minutes, the content of the flask is cooled down to the temperature lower than $-78°$ C. again, then trimethylsilyl methacrylic acid was added and stirred for two hours. The color of the content was turned to transparent. The reaction was stopped by adding ethanol, then 1.5 N diluted hydrochloric acid was added and deprotected. After evaporated off the solvent, the reacted product was dissolved by small amount of benzene, dropped in large amount of methanol and re-crystallized. The insoluble portion was removed and methanol was concentrated, then dropped into large amount of benzene and was re-crystallized. By drying the insoluble portion by vacuum for 3 hours at 80° C., polymer of white powder was separated (corresponding to M of FIG. 1).

Physical property of polymer: white powder solid; $Mn=2.4 \times 10^4$, $Mw/Mn=1.07$ (GPC polystyrene standard);
$^1$H NMR ($D_2O$, 300 MHz) 0.08 (brs), 0.87-1.26 (Br); $^{13}$CNMR ($D_2O$, 75.4 MHz) δ 17.2, 45.4, 49.2, 184.5; IR (KBr) 1702 (—COOH) cm.sup.−1.

Synthesis of a shell cross-linked micelle of poly(1,1-dimethyl-2,2-dihexyldisilanilene)-block-polymethacrylic acid 100 mg of block copolymer was put into 50 mL egg plant type flask sealed by septum rubber and equipped with a magnetic stirrer, and 20 mL of pure water was added. 0.18 mg (0.21 mmol) of 2,2'-(ethyleledioxy)bis(ethylamine) and 0.23 mg (1.20 mmol) of 1-(3-dimethylaminopropyl)-3-ethylcarbodiimide were added and stirred at the room temperature. After the solution was dialyzed and dried, the aimed compound was obtained (corresponding to the preparation process of SCM by way of FIG. 1 V process).

Physical property of the micelle: white powder solid; $^1$H NMR ($D_2O$/THF-$d_3$, 300 MHz) 0.4-0.5 (brs-SiMe$_2$—), 1.15-1.68 (br, SiHex$_2$-), 2.08 (brs-CH$_2$—C); $^{13}$CNMR ($D_2O$/THF-$d_3$, 75.4 MHz)δ 18.6, 44.8, 54.3, 166, 177; Solid-state CPMAS Si NMR-35.7, −27.6; IR (KBr) 3600-2500 (—OH), 1710 (—COOH), 1610, 1569cm$^{-1}$.

Reducing Reaction of Gold Ions using Polysilane Shell Cross-Linked Micelle (SCM) as a Template 1.76 g of polysilane cross-linked micelle and 7.0 mL of water were added to Bial and stirred well so as to prepare aqueous solution. 1.99 g of tetrachloroaurate(III)tetrahydrate dissolved in 3 mL of water was added to the solution and reacted with continuous stirring. When two solutions were mixed together, the color was turned slowly from yellow to violet. By the Uw visible absorption spectrum of the reacted mixture, the absorption at 540 nm originated to fine particles of gold was observed. From the measuring result of the distribution of particles by dynamic light scattering, the particle size in water is 22.6 nm (corresponding to MR of FIG. 1)

Figure 2:
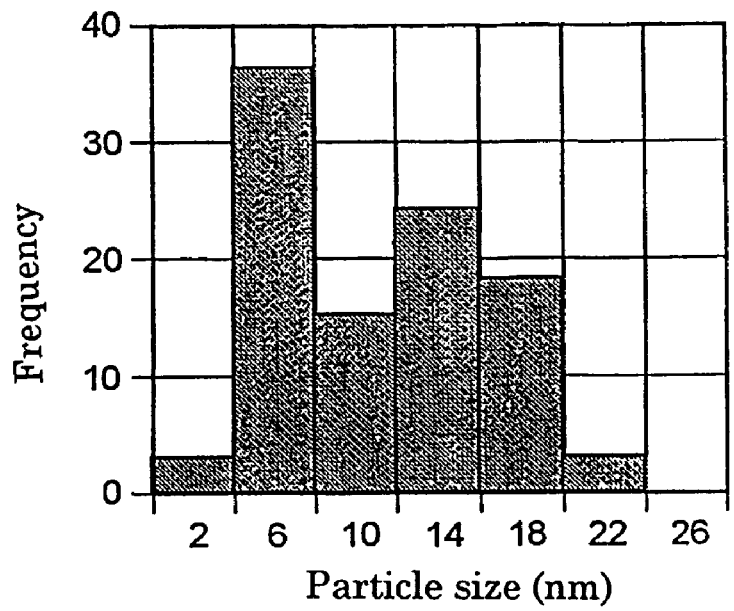
FIG. 2 shows the distribution curve of golden nano particles obtained in Example 1, according to the plan view of FIG. 1 showing the preparation process of metallic nano particles.
Figure 3:
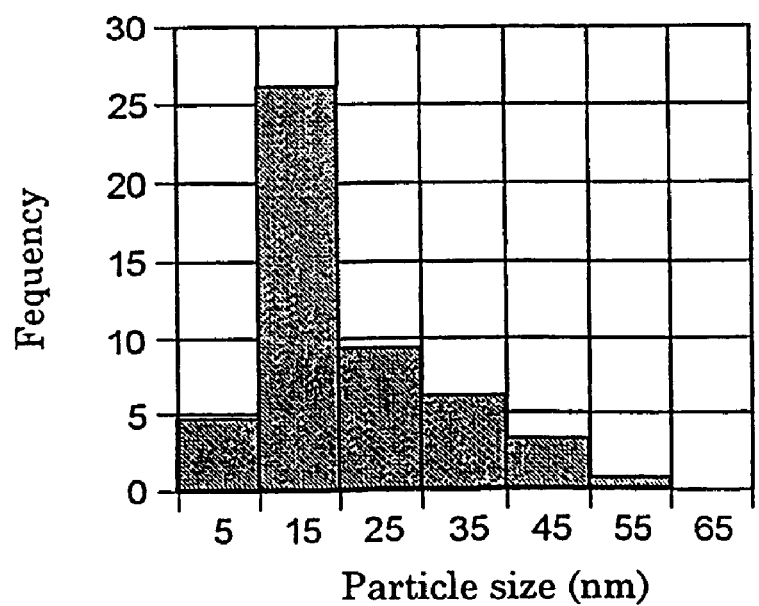
FIG. 3 shows the distribution curve of palladium nano particles obtained in Example 2

FIG. 1 show the model of the method for preparation of metallic nano particle using the shell cross-linked micelle (SCM) as a template. The distribution curve of the obtained gold nano particles is shown in FIG. 2. The particle size of the fine particles of gold measured by a transmission electron microscope is 11.1 nm by averaged value.

Average particle size: 11.1 nm
Standard deviation: 5

Example 2

Reducing Reaction of Palladium Ion using the Polysilane Shell Cross-Linked Micelle (SCM) used in Example 1 as a Template 1.1 g of polysilane cross-linked micelle and 2.0 mL of water were added to Bial and stirred well so as to prepare aqueous solution. 1.56 g of palladium chloride (II) sodium dissolved in 1.0 mL of water was added to the solution and reacted with continuous stirring. When two solutions were mixed together, the color was turned slowly from yellow to transparent and became colloidal solution. The particle size of the fine particles of palladium measured by a transmission electron microscope is 20.1 nm by averaged value.

Average particle size: 20.1 nm
Standard deviation: 11

Comparative Example

Reducing Reaction of Gold Ions using Polysilane Micelle (Not Cross-Linked) as a Template 1.76 g of polysilane cross-linked micelle synthesized in Example 1 and 7.0 mL of water were added to Bial and stirred well so as to prepare aqueous solution. 1.99 g of tetrachloroaurate(III)tetrahydrate dissolved in 3 mL of water was added to the solution and reacted with continuous stirring. When the reaction was started, the color was turned slowly from yellow to violet. By the UV visible absorption spectrum of the reacted mixture, the absorption at 550nm originated to fine particles of gold was observed. The particle size of the fine particles of gold measured by a transmission electron microscope is 25.4 nm by averaged value.

Average particle size: 25.4 nm
Standard deviation: 15

Figure 4:
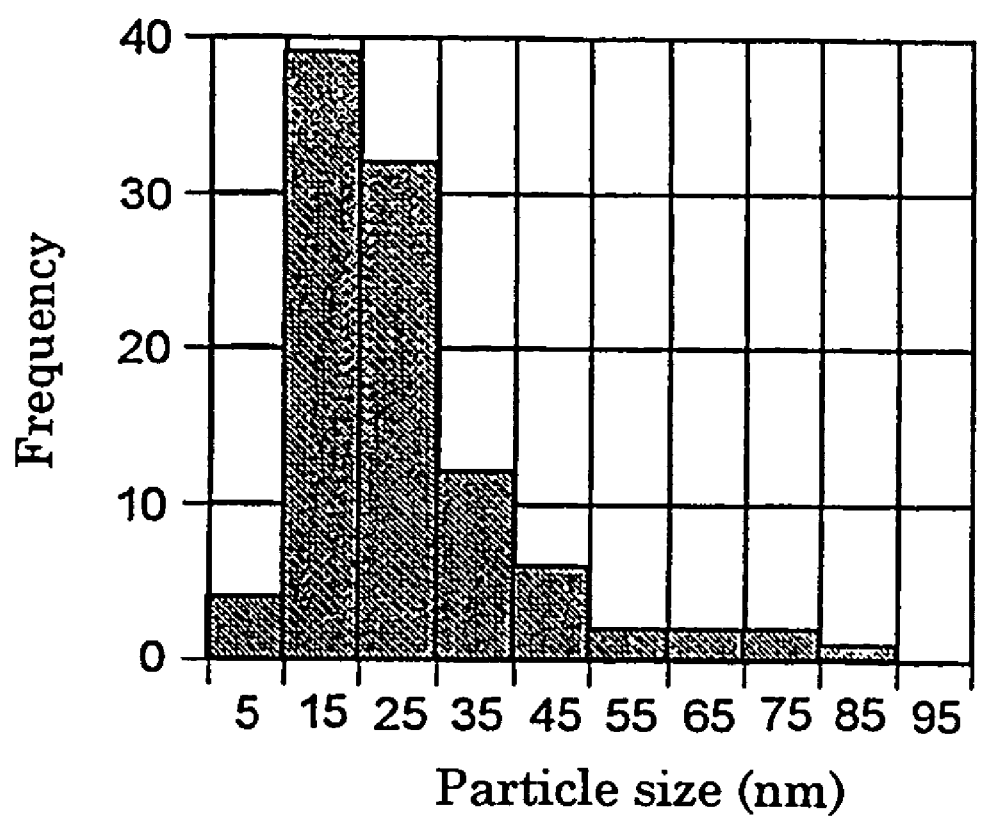
FIG. 4 shows the distribution curve of golden nano particles obtained in Comparative Example.

In the case when uncross-linked polymer micelle is used, the reducing reaction of metallic ions can be carried, however, as shown in the histogram of FIG. 4, the particle size of the prepared particles are large and the distribution of particle size is also large. When the standard deviations are compared, in the case when the cross-linked micelle is used is 5, and in the case when the uncross-linked micelle is used is 15, that is, distribution of particle size is largely different.

INDUSTRIAL APPLICABILITY

By the present invention, the method for preparation of metallic nano particles closely to monodispersion and have various uses are provided.

The present invention is to provide the method for preparation of metallic nano particles of monodispersion having various uses. The feature of the present invention is to reduce metallic ions using a shell cross-linked micelle (SCM) obtained by cross-linking hydrophilic micelle obtained from polysilane and hydrophilic polymer, especially polymethacrylic acid, using adequate cross-linking agent as a template, and by this method, nano size particles of metal having controlled particle size and dispersed stable in water can be obtained without using other reducing agent except above mentioned SCM.

What is claimed is:

1. A method for preparation of monodispersed fine particles of metal comprising, reducing metallic ions by means of a reducing agent, wherein the reducing agent is a hydrophilic micelle having polysilane, said hydrophilic micelle being obtained from a block copolymer composed of a hydrophilic polymer and a polysilane, said polysilane being represented by general formula P-1 wherein said polysilane is disposed on an inside of said micelle, and wherein a shell part of the micelle is formed by cross-linking the hydrophilic polymer, general formula P-1

wherein, $R_1$, $R_2$, $R_3$, and $R_4$ are the group selected independently from the group consisting of alkyl group of carbon number 10 or less and aryl group, m is the degree of polymerization of the polysilane, n is the degree of polymerization of a monomer component having a cross-linking hydrophilic group of the block copolymer, and n is such that the range of the molecular weight of the block polymer is Mn=7000-30000 wherein the ratio of n/m is from 10 to 20, and the ratio of m/n is from 0.05 to 0.10.

2. The method for, preparation of monodispersed fine particles of metal of claim 1, wherein the cross-linking agent is a compound selected from the compounds represented by general formula B, general formula B

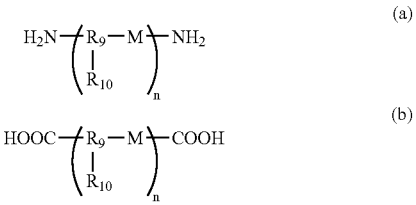

wherein, $R_9$ is alkylene chain of carbon number 4 or less, $R_{10}$ is functional group which substitute H of alkylene providing function to the obtained dispersion of fine particles of metal, p is from 2 to 30, M is oxygen, nitrogen or sulfur.

3. The method for preparation of monodispersed fine particles of metal of claim 2, wherein the cross-linking agent represented by general formula B contains in part poly (oxyalkylene) derivatives and, wherein M is oxygen and $R_9$ is alkylene group of carbon number 4 or less.

4. The method for preparation of monodispersed fine particles of metal of claim 1, wherein the hydrophilic micelle is formed by forming a micelle in aqueous medium with amphipathic block copolymer represented by general formula PB, said amphipathic block copolymer obtained by block copolymerization of anionic polymerizable monomer possessing polysilane and at least hydrophilic side chain with hydrophilic polymer containing hydrophilic polymer component, and cross-linking the shell of said micelle by hydrophilic group of the hydrophilic side chain, general formula PB

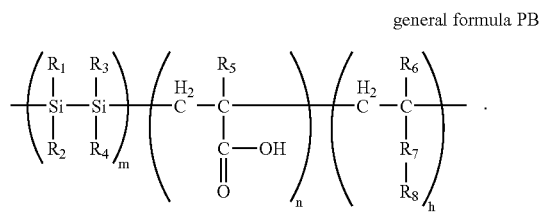

wherein; $R_1$, $R_2$, $R_3$, $R_4$, and m are same as of general formula P-1 of claim 1 and n is the same as in claim 1, $R_5$ and $R_6$ are H or lower alkyl group, $R_7$ is a divalent organic group or —COOR—, wherein R is alkylene group of carbon number 3 or less, or phenylene group, $R_8$ is COOH or OH group, h indicates copolymer component forming hydrophilic polymer with n', wherein h+n' is in the range from 0 to n, the value of n is in the range not disrupting the hydrophilicity of the shell.

5. The method for preparation of monodispersed fine particles of metal of claim 4, wherein the cross-linking agent is a compound selected from the compounds represented by general formula B, general formula B formula 1

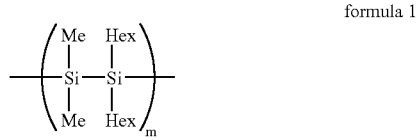

wherein, $R_9$ is alkylene chain of carbon number 4 or less, $R_{10}$ is functional group which substitute H of alkylene providing function to the obtained dispersion of fine particles of metal, p is from 2 to 30, M is oxygen, nitrogen or sulfur.

6. The method for preparation of monodispersed fine particles of metal of claim 5, wherein the cross-linking agent represented by general formula B contains in part poly (oxyalkylene) derivatives and, wherein M is oxygen and $R_9$ is alkylene group of carbon number 4 or less.

7. The method for preparation of monodisDersed fine particles of metal of claim 4, wherein the polysilane unit is represented by formula 1, formula 1

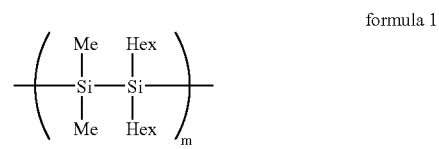

wherein, Me is methyl group, Hex is hexyl group.

8. The method for preparation of monodispersed fine particles of metal of claim 7, wherein the cross-linking agent is a compound selected from the compounds represented by general formula B general formula B

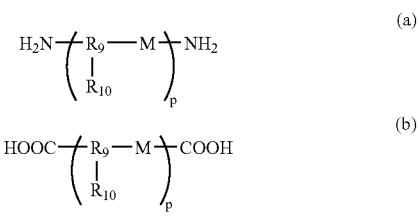

wherein, $R_9$ is alkylene chain of carbon number 4 or less, $R_{10}$ is functional group which substitute H of alkylene providing function to the obtained dispersion of fine particles of metal, p is from 2 to 30, M is oxygen, nitrogen or sulfur.

9. The method for preparation of monodispersed fine particles of metal of claim 8, wherein the cross-linking agent represented by general formula B contains in part poly (oxyalkylene) derivatives and, wherein M is oxygen and $R_9$ is alkylene group of carbon number 4 or less.

* * * * *

UNITED STATES PATENT AND TRADEMARK OFFICE
CERTIFICATE OF CORRECTION

PATENT NO. : 7,241,814 B2
APPLICATION NO. : 10/491133
DATED : July 10, 2007
INVENTOR(S) : Sanji Sakurai It is certified that error appears in the above-identified patent and that said Letters Patent is hereby corrected as shown below:

In claim 1, col. 8 line 33 replace in the general formula P-1 "SI" with --Si--.

In claim 2, col. 8 line 47 delete the comma between "for" and "preparation" in line 1.

In claim 4, col. 9 line 19 replace the term "mare" with the phrase --m are--.

In claim 5, col. 9 replace formula B with the following formulas (a) and (b) provided below:

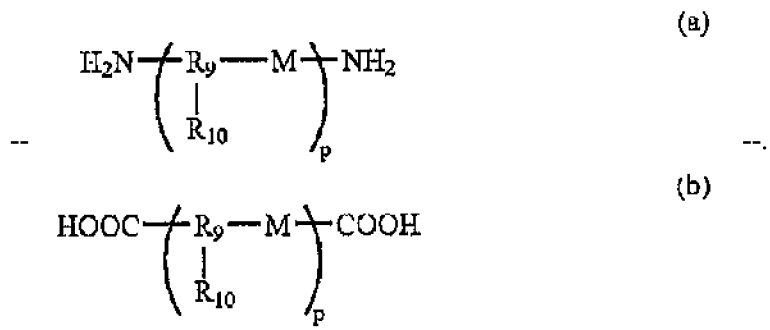

In claim 7, col. 10 line 1, replace the term "monodisDersed" with --monodispersed--.

Signed and Sealed this

Second Day of October, 2007

JON W. DUDAS
*Director of the United States Patent and Trademark Office*

UNITED STATES PATENT AND TRADEMARK OFFICE
CERTIFICATE OF CORRECTION

PATENT NO.       : 7,241,814 B2
APPLICATION NO.  : 10/491133
DATED            : July 10, 2007
INVENTOR(S)      : Sanji Sakurai Page 1 of 1

It is certified that error appears in the above-identified patent and that said Letters Patent is hereby corrected as shown below:

In the specification, col. 4, line 4, replace "n" in the general formula PB with --n' --.

Col. 9 Line 25
In claim 4, replace the "n" variable in the general formula PB with --n' --.

Signed and Sealed this

Eleventh Day of December, 2007

JON W. DUDAS
*Director of the United States Patent and Trademark Office*